US00PP28034P3

(12) United States Plant Patent
Tidmore

(10) Patent No.: US PP28,034 P3
(45) Date of Patent: May 16, 2017

(54) ***AGAPANTHUS* PLANT NAMED 'NEVERLAND'**

(50) Latin Name: *Agapanthus africanus*
Varietal Denomination: Neverland

(71) Applicant: Greenleaf Nursery Company, Park Hill, OK (US)

(72) Inventor: Ronald D. Tidmore, El Campo, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 82 days.

(21) Appl. No.: 14/756,034

(22) Filed: Jul. 23, 2015

(65) Prior Publication Data

US 2017/0027095 P1 Jan. 26, 2017

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Anne Grunberg
(74) *Attorney, Agent, or Firm* — Bethany R. Roahrig; James M. Weatherly; Cochran Freund & Young, LLC

(57) ABSTRACT

A new cultivar of *Agapanthus* plant named 'Neverland' that is characterized by a compact habit, moderate vigor, variegated leaves with yellow-green margins and mid-green central stripe, and bicolored pale-lilac and mid-blue flowers, is disclosed. In combination these traits set 'Neverland' apart from all other existing varieties of *Agapanthus* known to the inventor.

3 Drawing Sheets

Genus and species: *Agapanthus africanus*.
Variety denomination: 'Neverland'.

BACKGROUND

The present disclosure relates to a new and distinct cultivar of *Agapanthus* plant, also known as lily-of-the-Nile, which is grown as an ornamental plant for use in containers and in the landscape. The new cultivar, from the family Amaryllidaceae, is known botanically as *Agapanthus africanus* and will be hereinafter referred to as 'Neverland'.

'Neverland' was discovered by the inventor in 2003 in El Campo, Tex. as a single seedling within a commercially grown seed-raised crop of *Agapanthus* 'Peter Pan' (unpatented). Whereas 'Peter Pan' exhibits entirely green foliage, the new variety 'Neverland' exhibits variegated leaves consisting of yellow-green margins and mid-green center stripes.

Upon discovery of the single variegated seedling, the inventor removed and transplanted the seedling into a nursery liner container for further observation and overwintering. In spring 2004, the inventor potted the liner transplant into a 1 gallon container in order to observe the stability of the variegation in the foliage and also the flowering characteristics. During 2005 or 2006, the inventor potted the 1 gallon container plant into a 3 gallon container. During 2009, the inventor first asexually propagated the variegated plant by multiple division, with further divisions in each subsequent year in El Campo, Tex. 'Neverland' is stable and reproduces true to type in successive generations of asexual reproduction.

SUMMARY

The following traits have been repeatedly observed and represent the distinguishing characteristics of 'Neverland'.

'Neverland' has not been tested under all possible conditions and phenotypic differences may be observed with variations in environmental, climatic, and cultural conditions, without however, any variance in genotype.

1. 'Neverland' exhibits a compact habit;
2. The flowers of 'Neverland' is moderately vigorous, allowing four to six divisions after one year of growth in a one gallon container.
3. 'Neverland' exhibits variegated strap-like leaves.
4. The leaf variegation of 'Neverland' consists of a yellow-green margin with a mid-green central stripe.
5. 'Neverland' produces blooms in succession from spring until late summer and into fall where daytime temperatures are sustained above 20° C.
6. The flowers of 'Neverland' are comprised of bicolored petals (tepals) which are predominantly pale lilac in color, with a mid-blue center.
7. 'Neverland' is 0.3 meters in height and width after one year of growth in a one gallon container.
8. 'Neverland' remains at 0.3 meters in height in subsequent years or in larger containers, although the width of 'Neverland' increases with age.
9. 'Neverland' is hardy in USDA Zones 7 to 10.
10. 'Neverland' requires shade or filtered sunlight, well-draining soil, and low to moderate water.

DESCRIPTION OF THE PHOTOGRAPHS

The accompanying color photographs illustrate the overall appearance of the new *Agapanthus* cultivar 'Neverland' showing the colors as true as it is reasonably possible to obtain in colored reproductions of this type. Photographs were taken in El Campo, Tex. of 24-month old plants grown outdoors in three gallon containers. Colors in the photographs may differ from the color values cited in the detailed botanical description, which more accurately describes the actual colors of the new variety 'Neverland'.

DESCRIPTION OF THE NEW VARIETY

Figure 1:
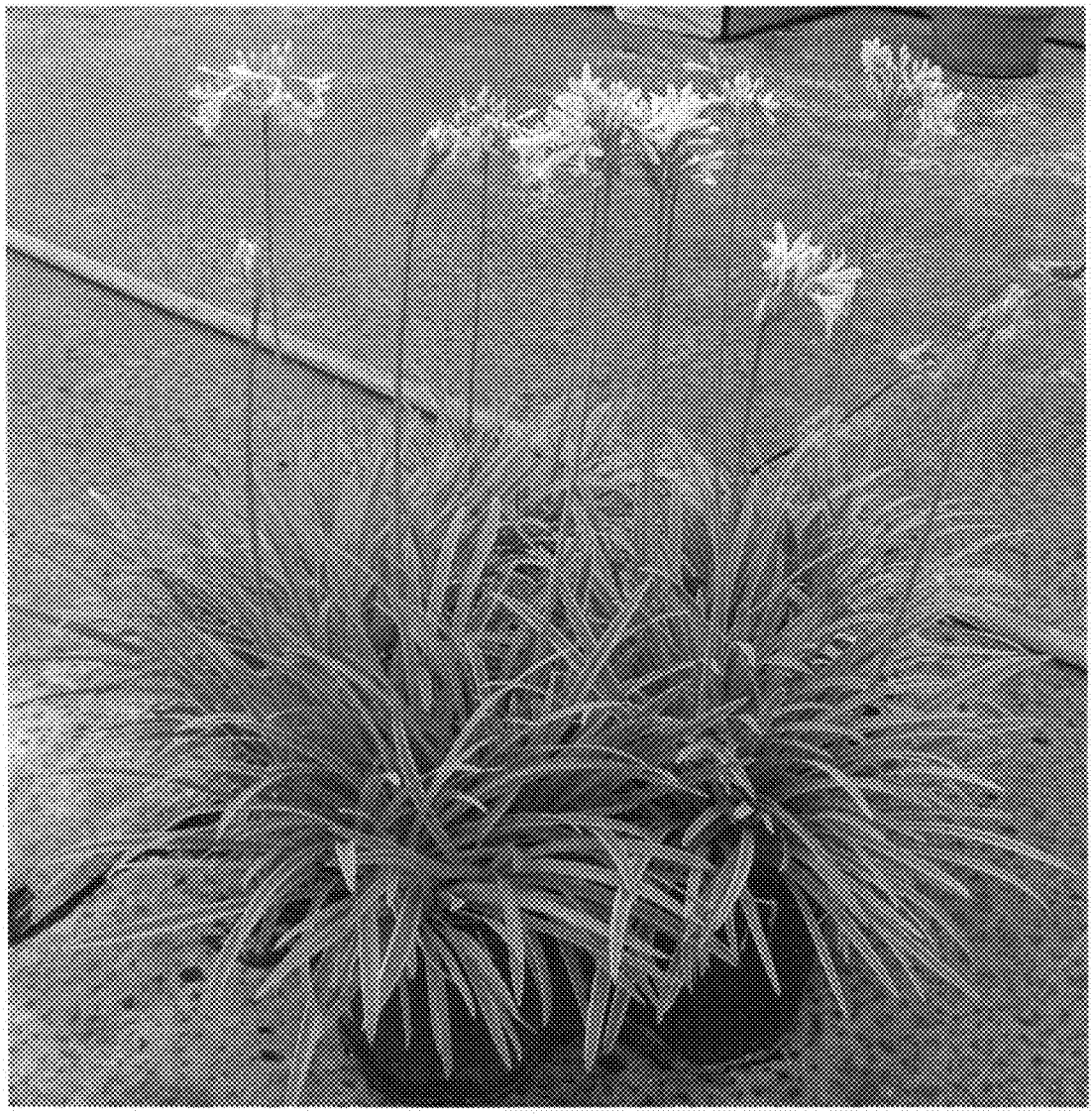
FIG. 1 depicts two whole plants of 'Neverland' grown in a three gallon container and flowering for the first time.
Figure 2:
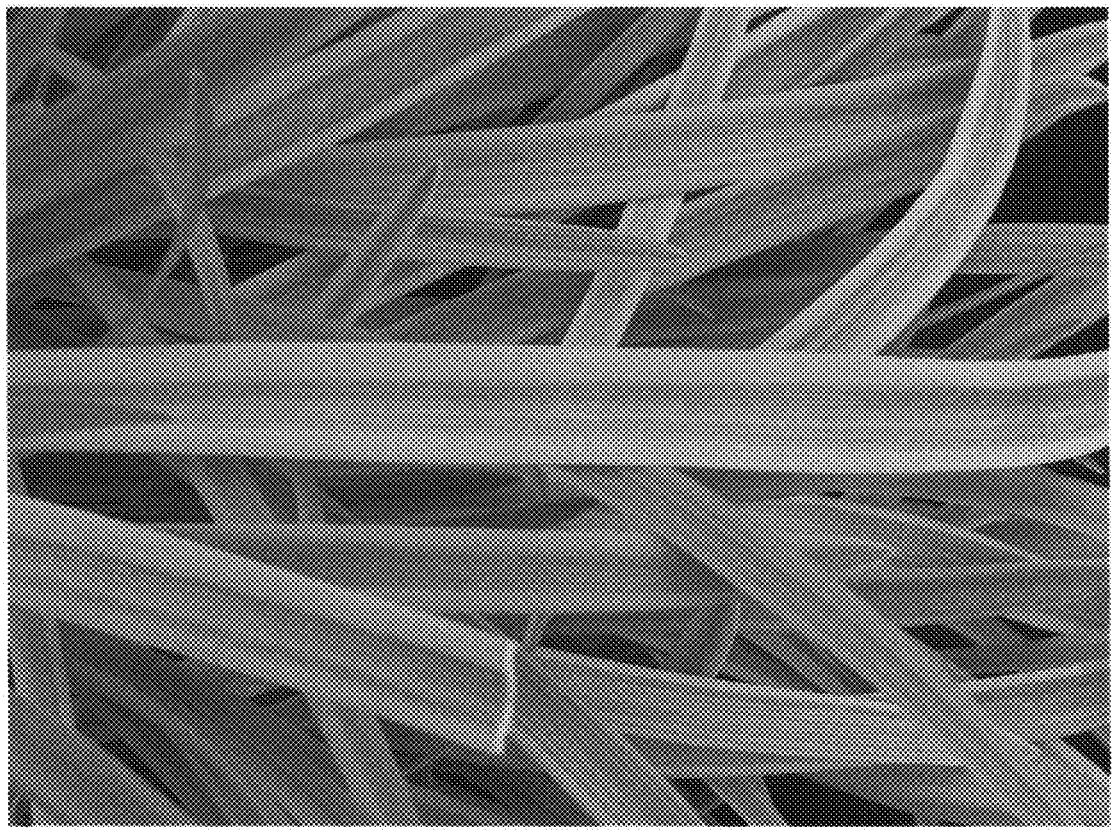
FIG. 2 depicts a close-up view of the variegated foliage of 'Neverland'.
Figure 3:
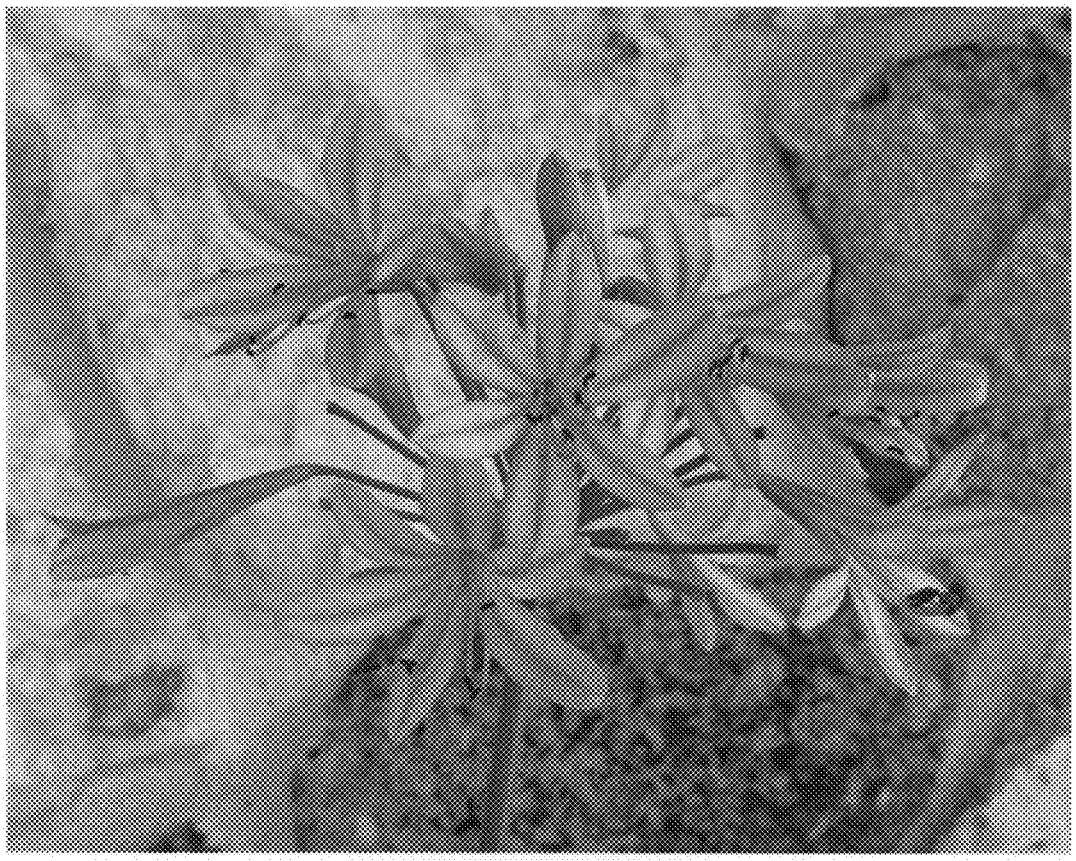
FIG. 3 depicts a close-up view of the inflorescence of 'Neverland'.

The following detailed descriptions set forth the distinctive characteristics of 'Neverland'. Observations, measurements, values, and comparisons were collected from plants grown outdoors in El Campo Tex. The plants were 24-months old from a division and were growing in three gallon containers. Additional descriptions were taken from a single plant established in a private garden in Santa Barbara, Calif. grown under conditions of high light, low humidity and minimal water. Under these latter conditions, 'Neverland' has been observed to grow with reduced vigor and reduced overall height. In addition, the colors of the flowers of 'Neverland' appear to have been intensified by the hot dry conditions. Where applicable, color readings in Santa Barbara, Calif. are identified in the description below. Color determinations were made in accordance with The 2007 Royal Horticultural Society Colour Chart from London England, except where general color terms of ordinary dictionary significance are used.

Classification:

*Family.*—Amaryllidaceae.

*Genus.*—*Agapanthus.*

*Species.*—*Africanus.*

*Common name.*—Lily-of-the-Nile or Dwarf Lily-of-the-Nile.

Parentage: *Agapanthus africanus* 'Neverland' arose as a chance seedling discovered in a commercial seedling crop of *Agapanthus africanus* 'Peter Pan' (unpatented).

Plant:

*Use.*—Ornamental for use in containers and in the landscape.

*Type.*—Perennial bulb.

*Vigor.*—Moderate.

*Habit.*—Compact; foliage initially semi-erect become mounding and weeping.

*Plant dimensions* (*after one year,* 1 *gallon container*).—55 cm to 60 cm in height including inflorescence; 30 cm in width.

*Plant dimensions* (*at maturity,* 3 *gallon container*).—55 cm to 60 cm in height including inflorescence; 40 cm to 50 cm in width.

*Hardiness.*—Hardy in USDA Zones 7 to 10.

*Propagation.*—Asexual propagation is accomplished by division.

*Root system.*—Thick and fleshy.

*Cultural requirements.*—Well-draining soil, shade to filtered sunlight in order to avoid photo-bleaching in high light conditions, and low to moderate water.

*Cropping time* (*range*).—6 to 9 months to produce a flowering 1 gallon container plant from division; 12 to 15 months if produced in a 3 gallon container.

*Seasonal interest.*—Flowers in spring and summer, and variegated foliage year round.

Foliage:

*Foliage type.*—Evergreen.

*Foliage canopy dimensions.*—30 cm in height from soil surface; 30 cm in width after one year, 40 cm to 50 cm in width at maturity.

*Leaf shape.*—Lorate.

*Leaf quantity* (*range*).—65 to 70 leaves per plant.

*Leaf form.*—Arching.

*Leaf branching.*—Basal.

*Leaf attachment.*—Sheathing.

*Leaf apex.*—Acute.

*Leaf base.*—Truncate.

*Leaf division.*—Simple.

*Leaf margin.*—Entire.

*Leaf color* (*both surfaces*).—Outer margins of leaf blade range between N144D and 154B; center of leaf blades ranges between 137A and 137B, with occasional longitudinal striations of N144D to 154B as margins.

*Leaf surface* (*adaxial and abaxial surfaces*).—Glabrous.

*Venation pattern.*—Parallel.

*Vein color* (*abaxial and adaxial surfaces*).—Very faint 144B in outer margins and faint 138C in center.

*Leaf dimensions* (*fully developed*).—35 cm in length and 1.6 cm maximum width.

*Leaf fragrance.*—None observed.

Inflorescence:

*Blooming months.*—March through September.

*Inflorescence type.*—Single umbel.

*Dimensions of inflorescence* (*average*).—12 cm to 15 cm in width and 8 cm to 9 cm in height.

*Flower quantity* (*mid-season in full flower*).—Between 60 and 80 flowers per umbel.

*Persistent or self-cleaning.*—Self-cleaning.

*Flower aspect within umbel.*—Facing outward, ranging between 30° below the horizontal to 45° above the horizontal.

*Scape or peduncle.*—Leafless flower stem emerging from base of plant. Scape shape: Cylindrical. Scape texture: Pithy. Scape surface: Glabrous. Scape color: Ranges between 136C and 137A. Scape strength: Strong. Scape dimensions: 45 cm to 50 cm in length and 4 mm to 5 mm in diameter.

*Pedicel.*—Pedicel color: Range between 136C and 137A. Pedicel dimensions: 3 cm to 4 cm in length and 2 mm in diameter. Pedicel surface: Glabrous.

*Bud.*—Bud shape: Obelliptic. Bud color: 97D; in Santa Barbara, Calif. color is 93C. Bud dimensions (average): 8 mm in length and 5 mm in diameter. Bud apex: Rounded. Bud base: Cuneate. Bud surface: Glabrous.

*Flower shape.*—Funnel; unfused tepals widely flared.

*Flower dimensions.*—3.5 cm in depth and 3.5 cm in diameter.

*Petals.*—Apetalous.

*Tepal quantity.*—6. Fused or unfused: Basally fused for one third of length. Tepal shape: Oblanceolate. Tepal margin: Entire. Tepal surfaces (abaxial and adaxial): Glabrous. Tepal color (adaxial surface): Predominantly 95D, except central longitudinal stripe of 95C. Tepal color (abaxial surface): 95C. Tepal color in Santa Barbara, Calif. (adaxial and abaxial surfaces): 97A. except central longitudinal stripe 96B. Tepal dimensions: 3.5 cm in length and 6 mm to 8 mm in width. Tepal apex: Apiculate.

*Flower fragrance.*—None observed.

Reproductive organs:

*Stamens.*—Stamen quantity: 6, adnate to corolla tube. Stamen color: 95B except pale light blue nearest to 106D at base. Stamen dimensions: 1.7 cm in length and 1 mm in diameter. Anther: Anther color: N186C and N200A have both been observed on individual anthers. Anther shape, attachment: Clavate, dorsifixed. Anther dimensions: 2 mm in length, 0.8 mm in width. Pollen color: 7A. Pollen quantity: Sparse, absent on some anthers.

*Pistil.*—Pistil quantity: One. Pistil color: 95B. Pistil dimensions: 1.5 cm in length and 1 mm in diameter. Stigma: Minute, capitate, diameter less than 1 mm. Stigma color: 156D. Ovary: Ovary color: 151D. Ovary shape: Trigonous. Ovary dimensions: 8 mm in height and 3 mm in width. Ovary position: Superior.

Fruit: Only immature fruit has been observed.

*Quantity.*—Sparse, most flowers abort.

*Fruit shape.*—Trigonous capsule with three locules.

*Fruit dimensions.*—2 cm in length and 7 mm in width.

*Fruit color.*—144A becoming 146A.

Seed: Seed has only been observed within immature fruit.

*Quantity.*—10 to 14 seeds per locule; 30 to 45 seeds per fruit.

*Shape.*—Ovoid, flattened with papery wing.

*Dimensions.*—2.5 mm in length, 1.5 mm in width.

*Color.*—155C.

Disease susceptibility: Susceptible to *Pythium* spp. and *Phytophthora* spp. Root and stem rots.

Pest susceptibility: Protect from slugs and snails.

COMPARISON WITH PARENTAL LINE AND KNOWN VARIETIES

'Neverland' is distinguishable from the parent, 'Peter Pan' as follows. Whereas 'Peter Pan' exhibits entirely green foliage, the new variety 'Neverland' exhibits yellow-green and mid-green variegated foliage. In addition, when comparing plants of like age and production schedule, 'Neverland' is slightly shorter in overall height (including the flowers) and slightly less vigorous in its multiplication than 'Peter Pan'.

'Neverland' may also be compared with the variegated variety 'Hinag' (U.S. Plant Pat. No. 10,866). Whereas the foliage of 'Hinag' is variegated with golden yellow margins and dark olive-green central stripes, the margins of 'Neverland' are yellow-green in color and the central stripes are mid-green in color. In addition, in comparison with 'Neverland', 'Hinag' is a larger and more vigorous plant, with longer and wider leaves.

'Neverland' may also be compared with the variegated variety 'Tinkerbell' (unpatented). The *Agapanthus* variety 'Tinkerbell' exhibits cream-white leaf margins, whereas the margins of 'Neverland' are green-yellow in color.

I claim:

1. A new and distinct cultivar of *Agapanthus* plant named 'Neverland' as described and illustrated herein.

* * * * *